United States Patent [19]

Baggiolini et al.

[11] Patent Number: 5,612,328

[45] Date of Patent: Mar. 18, 1997

[54] VITAMIN D3 FLUORINATED ANALOGS

[75] Inventors: Barbara J. Baggiolini, North Caldwell; Shian-Jan Shiuey, Nutley; Milan R. Uskokovic, Upper Montclair, all of N.J.

[73] Assignee: Hoffmann-La Roche Inc., Nutley, N.J.

[21] Appl. No.: 595,373

[22] Filed: Feb. 1, 1996

Related U.S. Application Data

[62] Division of Ser. No. 419,796, Apr. 11, 1995, Pat. No. 5,512,554, which is a division of Ser. No. 184,082, Jan. 18, 1994, Pat. No. 5,451,574, which is a continuation of Ser. No. 971,788, Nov. 5, 1992, abandoned, which is a continuation-in-part of Ser. No. 957,500, Oct. 7, 1992, abandoned.

[51] Int. Cl.$^6$ .................................................. A61K 31/59
[52] U.S. Cl. ............................................ 514/167; 552/653
[58] Field of Search ............................................. 514/167

[56] References Cited

U.S. PATENT DOCUMENTS 5,428,029   6/1995   Doran et al. ............................. 514/167

*Primary Examiner*—Kimberly J. Prior
*Attorney, Agent, or Firm*—George W. Johnston; Ellen Ciambrone Coletti

[57] ABSTRACT

Compounds of the formula

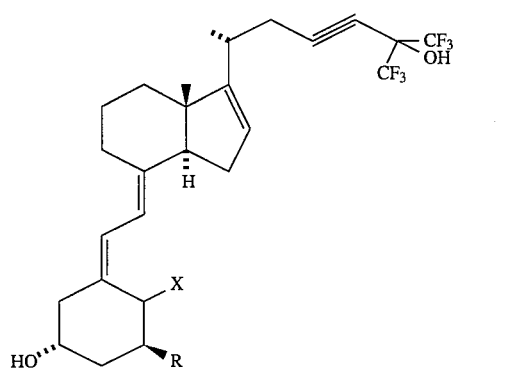

wherein R is hydrogen, hydroxy, or fluorine, and X is $H_2$ or $=CH_2$ are useful as agents for the treatment of hyperproliferative disorders of the skin such as psoriasis, as agents for the treatment of cancer, such as, leukemia, and as agents for the treatment of sebaceous gland diseases, such as, acne and seborrheic dermatitis.

6 Claims, No Drawings

VITAMIN D3 FLUORINATED ANALOGS

RELATED APPLICATION

This is a division, of application Ser. No. 08/419,796, filed Apr. 11, 1995, now U.S. Pat. No. 5,512,554, which is a Rule 60 divisional of Ser. No. 08/184,082, filed Jan. 18, 1994, now U.S. Pat. No. 5,451,574, which is a Rule 60 continuation of Ser. No. 07/971,788, filed Nov. 5, 1992, now abandoned, which is a continuation-in-part of Ser. No. 07/957,500, filed Oct. 7, 1992, now abandoned.

BRIEF SUMMARY OF THE INVENTION

The invention relates to compounds of the formula

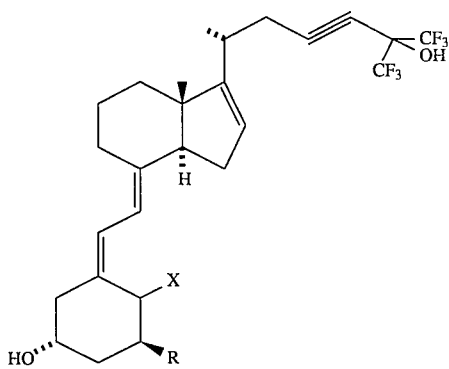

wherein R is hydrogen, hydroxy or fluorine and X is $H_2$ or $=CH_2$.

Compounds of formula I as described above are useful as agents for the treatment of hyperproliferative skin diseases such as psoriasis. Compounds of formula I as described above are also useful as agents for the treatment and prevention of leukemia and cancer. Compounds of formula I above are also useful as agents for the treatment of sebaceous gland diseases, such as, acne and seborrheic dermatitis.

DETAILED DESCRIPTION OF THE INVENTION

In the formulas presented herein, the various substituents are illustrated as joined to the nucleus by one of the following notations: a wedged solid line (◀) indicating a substituent which is above the plane of the molecule, and a wedged dotted line (⋯⋯) indicating a substituent which is below the plane of the molecule.

The invention relates to compounds of the formula

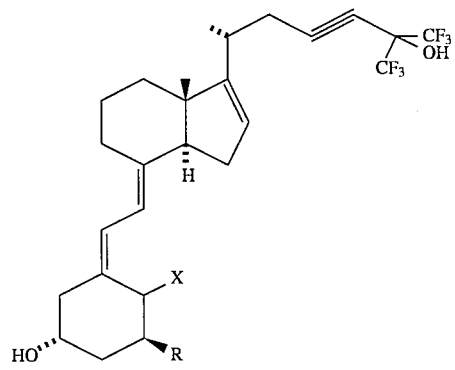

wherein R is hydrogen, hydroxy or fluorine and X is $H_2$ or $=OH_2$.

Compounds of formula I as described above stimulate differentiation and decrease proliferation of human keratinocytes. Accordingly, compounds of formula I as described above are useful as agents in the treatment of hyperproliferative skin disorders such as psoriasis, basal cell carcinomas, disorders of keratinization, and keratosis. The compounds of formula I are also useful as agents in the prevention and treatment of leukemia and cancer. The compounds of formula I are also useful for the treatment of sebaceous gland diseases, such as, acne and seborrheic dermatitis.

The invention also relates to a composition comprising a compound of formula I, or a mixture of two or more compounds of formula I.

The invention also relates to a method for treating the above-mentioned disease states by administration of a compound of formula I, or a mixture of two or more compounds of formula I.

The invention also relates to a process for preparing compounds of formula I as described above.

Exemplary compounds of formula I of the invention are:

26,26,26,27,27,27-hexafluoro-1α,25-dihydroxy-16-ene-23-yne-cholecalciferol;

26,26,26,27,27,27-hexafluoro-25-hydroxy-16-ene-23-yne-cholecalciferol;

26,26,26,27,27,27-hexafluoro-1α-fluoro-25-hydroxy-16-ene-23-yne-cholecalciferol;

26,26,26,27,27,27-hexafluoro-1α,25-dihydroxy-16-ene-23-yne-19-nor-cholecalciferol;

26,26,26,27,27,27-hexafluoro-25-hydroxy-16-ene-23-yne-19-nor-cholecalciferol; and 26,26,26,27,27,27-hexafluoro-1α-fluoro-25-hydroxy-16-ene-23-yne-19-nor-cholecalciferol.

In the compound of formula I, R is preferably hydroxy or fluorine.

Preferred compounds of formula I are:

26,26,26,27,27,27-hexafluoro-1α,25-dihydroxy-16-ene-23-yne-cholecalciferol;

26,26,26,27,27,27-hexafluoro-1α-fluoro-25-hydroxy-16-ene-23-yne-cholecalciferol; and 1,25-dihydroxy-16-ene-23-yne-26,26,26,27,27,27-hexafluoro-19-nor cholecalciferol.

The compounds of formula I are prepared as hereafter described, with particular reference to the Formula Schemes below.

SCHEME I

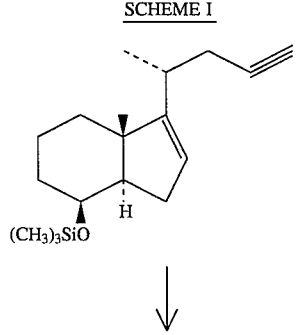

-continued
SCHEME I

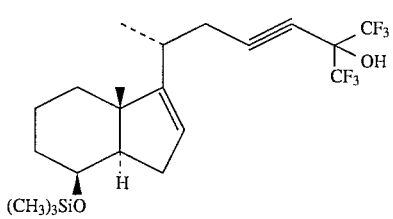

In above Formula Scheme I, the compound of formula II, a known compound, is converted to the compound of formula III by reaction with a base, such as, n-butyllithium, and hexafluoroacetone. The reaction is conducted in an ether solvent such as tetrahydrofuran at about −50° C. to about −100° C. The compound of formula III is recovered by quenching the reaction, followed by a conventional work-up and a purification as by chromatography.

SCHEME II

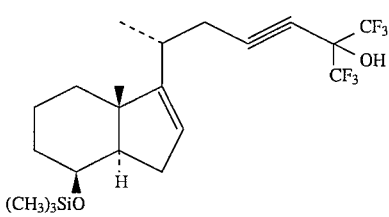

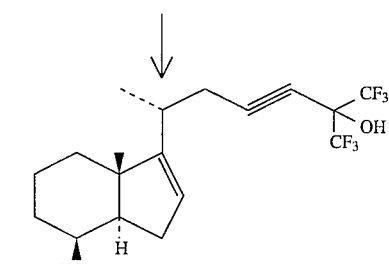

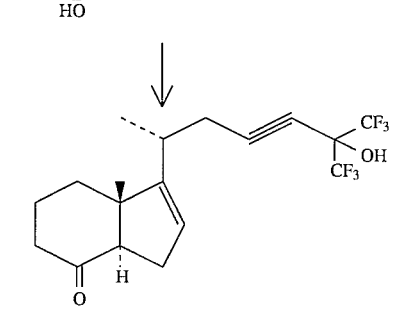

In reaction Scheme II, the compound of formula III is deprotected to give the compound of formula IV by reaction with tetrabutylammonium fluoride in an ether solvent such as, tetrahydrofuran.

The compound of formula IV is reacted with pyridinium chlorochromate in a chlorinated hydrocarbon solvent such as methylene chloride at room temperature to give the compound of formula V.

SCHEME III

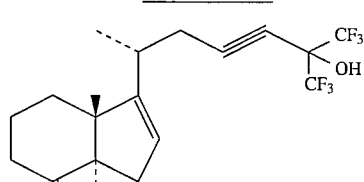

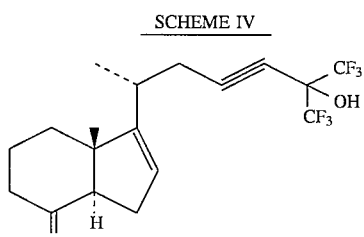

wherein t.Bu is tertiarybutyl and Ph is phenyl.

In formula scheme III, the compound of formula V is reacted with n-butyllithium and the compound of formula VI in a mixture of hexane and tetrahydrofuran at a temperature of −75° C. to give a compound of formula Ia after removal of silyl protecting groups with tetrabutylammonium fluoride in tetrahydrofuran solvent.

SCHEME IV

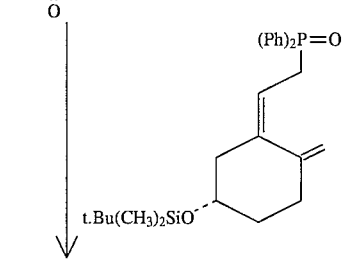

-continued
SCHEME IV

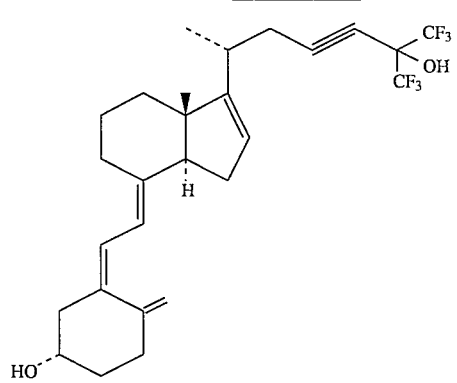

Ib wherein t.Bu is tertiarybutyl and Ph is phenyl.

In formula Scheme IV, the compound of formula V is reacted with n-butyllithium and the compound of formula VII in a mixture of hexane and tetrahydrofuran, at a temperature of −75° C. to give the compound of formula Ib after removal of the silyl protecting group with tetrabutylammonium fluoride in tetrahydrofuran solvent.

SCHEME V

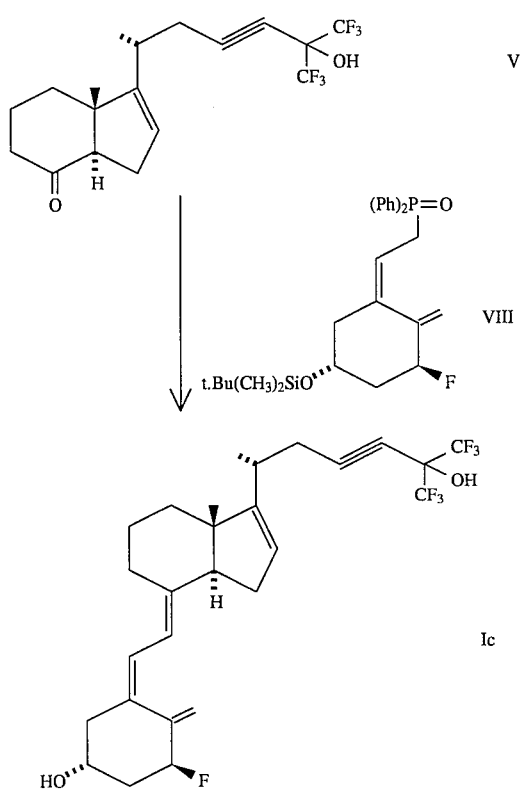

wherein t.Bu is tertiarybutyl and Ph is phenyl.

In formula Scheme V, the compound of formula V is reacted with n-butyllithium and the compound of formula VIII in a mixture of hexane and tetrahydrofuran solvent at a temperature of −75° C. to give the compound of formula Ic, after removal of the silyl protecting group with tetrabutylammonium fluoride in tetrahydrofuran solvent.

SCHEME VI

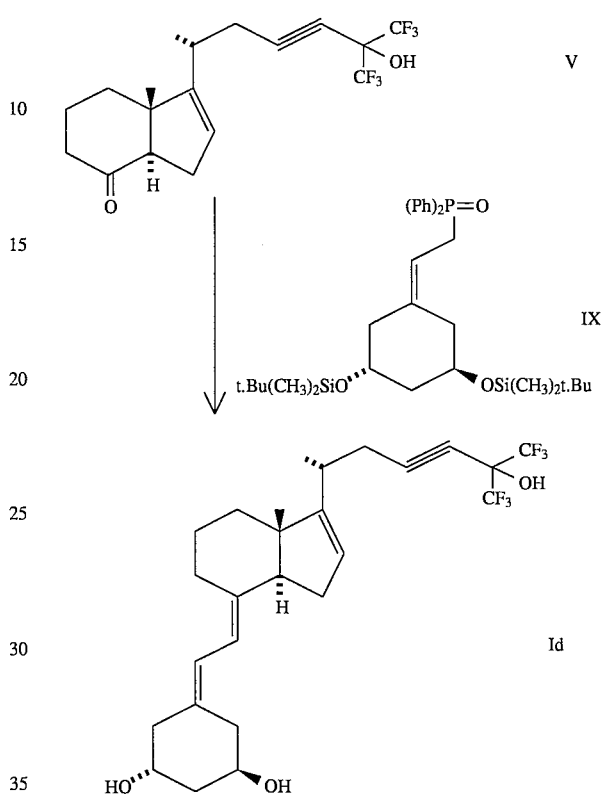

wherein t.Bu is tertiarybutyl and Ph is phenyl.

In formula Scheme VI, the compound of formula V is reacted with n-butyllithium and the compound of formula IX, a known compound, in a mixture of hexane and tetrahydrofuran solvent at a temperature of −75° C. to give the compound of formula Id, after removal of the silyl protecting group with tetrabutylammonium fluoride in tetrahydrofuran solvent.

SCHEME VII

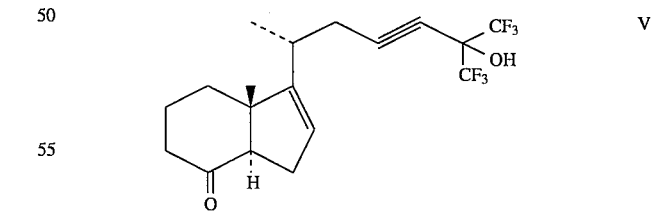

-continued
SCHEME VII

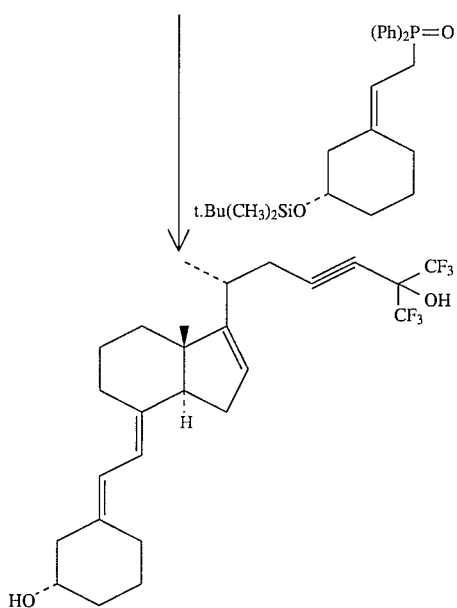

wherein t.Bu is tertiarybutyl and Ph is phenyl.

In formula Scheme VII, the compound of formula V is reacted with n-butyllithium and the compound of formula X, which can be prepared by known methods, in a mixture of hexane and tetrahydrofuran solvent at a temperature of −75° C. to give the compound of formula Ie, after removal of the silyl protecting group with tetrabutylammonium fluoride in tetrahydrofuran solvent.

SCHEME VIII

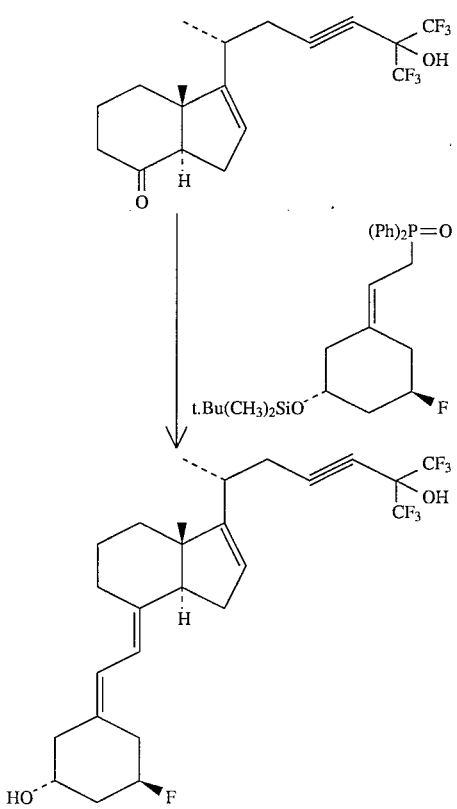

wherein t.Bu is tertiarybutyl and Ph is phenyl.

In formula Scheme VIII, the compound of formula V is reacted with n-butyllithium and the compound of formula XI, which can be prepared by known methods, in a mixture of hexane and tetrahydrofuran solvent at a temperature of −75° C. to give the compound of formula If, after removal of the silyl protecting group with tetrabutylammonium fluoride in tetrahydrofuran solvent.

The compounds of formula I as described above can be administered orally, for the treatment of neoplastic diseases such as leukemia, to warmblooded animals which need such treatment. More specifically, the compounds of formula I as described above can be administered orally to an adult human in dosages that are in the range of about 0.1 to 10 μg per day for the treatment of neoplastic diseases such as leukemia.

The compounds of formula I as described above, can be administered orally in an effective amount, for the treatment of hyperproliferative skin diseases such as psoriasis, basal cell carcinomas, disorders of keratinization, and keratosis, to warmblooded animals which need such treatment. Preferably, the compounds of formula I as described above can be administered orally to an adult human in dosages that are in the range of about 0.001 to 100 μg per day for the treatment of hyperproliferative skin diseases such as psoriasis, basal cell carcinomas, disorders of keratinization, and keratosis.

The compounds of formula I as described above, can be administered orally in an effective amount, for the treatment of sebaceous gland diseases such as acne and seborrheic dermatitis to a host requiring such treatment. Preferably, the compounds of formula I, as described above, can be administered orally to an adult human in dosages that are in the range of about 0.07 μg to 770 μg per day, more preferably in the range of about 0.7 μg to 70 μg per day for the treatment of sebaceous gland diseases, such as acne.

The compounds of formula I, as described above, can be administered topically in an effective amount, for the treatment of hyperproliferative skin diseases such as psoriasis, basal cell carcinomas, disorders of keratinization, and keratosis, to warmblooded animals which need such treatment. Preferably, the compounds of formula I as described above can be administered topically in dosages that are in the range of about 0.01 to about 100 μg per gram of topical formulation per day, for the treatment of hyperproliferative skin diseases such as psoriasis, basal cell carcinomas, disorders of keratinization, and keratosis.

The compounds of formula I, as described above, can be administered topically in an effective amount, for the treatment of sebaceous gland diseases, such as acne and seborrheic dermatitis, to a host in need of such treatment. Preferably, the compounds of formula I, as described above, can be administered topically in dosages that are in the range of about 0.1 to about 1000 μg per gram of topical formulation per day, for the treatment of sebaceous gland diseases, such as, acne and seborrheic dermatitis.

The useful activity of compounds of formula I as agents for the treatment of hyperproliferative skin diseases can be demonstrated by the following test procedures which are known in the art, and which are also set forth in Holick et al., The Society for Investigative Dermatology, p. 709–714 (1986).

Human Keratinocyte Antiproliferative Assay

Cells:

Primary or passage 1 subconfluent cultures of human neonatal keratinocytes were grown in Keratinocyte Growth Media® (KGM® modified MCDB 153, Clonetics, Inc.

Catalog #CC3001) supplemented with antibiotics or calcium chloride as needed. Cultures were obtained from neonatal foreskin epithelial keratinocytes using standard procedures.

Culture Conditions:

Human neonatal foreskins were collected by circumcision and placed into tubes containing Dulbecco's minimum essential Media (DMEM) with 10% serum. Upon arrival at the laboratory, they were mechanically trimmed of excess dermis, and treated with a solution of trypsin/ethylenediamine tetraacetic acid (EDTA) (0.05%/0.02%) at 4° C. overnight. The epidermis was stripped from the dermis, agitated in buffered saline to remove basal keratinocytes and the stratum corneum later removed. The separated cells were centrifuged, resuspended in media, counted, and the cells plated onto plastic culture dishes or flasks at 5,000 to 25,000 cells/cm$^2$ in KGM media according to protocols developed by Boyce and Ham, In Vitro Models for Cancer Research III, 246–274, (1986) for MCDB 153 media. The cultures are incubated in humidified chambers with 5% $CO_2$ at 37° C. with refeeding fresh media 2 to 3 times per week. Prior to reaching confluency, the cells are replated (called passage 1) at 25,000 cells/well on 6-well cluster plates (Costar catalog #3406) in KGM.

Antiproliferation Assay Protocol:

Approximately twenty-four hours after passage, the cells were refed with fresh KGM media supplemented to 1.5 mM $CaCl_2$ that contains test compound or vehicle. Solutions of test compounds were prepared as follows: 1 milligram quantities were received in amber glass vials and stored at −20° C. Sufficient 100% ethanol was added directly to vials to obtain a millimolar solution that was subsequently aliquoted into small amber vials, overlayed with argon gas and stored at −20° C. Each stock solution was thawed once, used and discarded. Stock solutions were used within 4 to 6 weeks. Aliquots from the stock solution were diluted directly into medium and then serially diluted from micromolar to picomolar concentrations. Compounds were typically tested at four concentrations in triplicate wells. Control wells are supplemented with vehicle alone at the highest concentration such as 0.1% ethanol. At the termination of the experiment prior to the cultures reaching confluency, the cells were enumerated by the following procedure. Dishes were washed with phosphate buffered saline, and then incubated with trypsin/EDTA solution for 30 minutes. Cells were suspended and an aliquot placed into isotonic buffered saline and counted on an electronic particle counter (Coulter Counter). The counter was periodically calibrated for the correct size of keratinocytes. Each well was counted in triplicate. The number of cell/dish was calculated according to dilution factors used and results are presented as percent inhibition from cell numbers obtained in control cultures. The results are set forth in Table I.

TABLE I

| | % Inhibition Dose (M) | | | |
|---|---|---|---|---|
| | $10^{-9}$ | $10^{-8}$ | $10^{-7}$ | $10^{-6}$ |
| 1,25-dihydroxy-16-ene-23-yne-26,27-hexafluorocholecalciferol | 99.6 ± 4.6 | 70.5 ± 8.5 | 45.6 ± 8.4 | 33.7 ± 8.8 |
| 25-hydroxy-16-ene-23-yne-26,27-hexafluorocholecalciferol | 119.2 ± 13.6 | 105.7 ± 12.1 | 75.7 ± 11.3 | 19.7 ± 5.3 |
| 1α-fluoro-25-hydroxy-16-ene-23-yne-26,27-hexafluorocholecalciferol | 95.5 ± 1.5 | 96.6 ± 1.7 | 53.4 ± 3.32 | 25.8 ± 3.6 |

1,25-dihydroxy-16-ene-23-yne-26,27-hexafluorocholecalciferol exhibited an average ED50 (Dose that would obtain 50% of the number of cells as compared to the control)=0.08 μM.

25-hydroxy-16-ene-23-yne-26,27-hexafluorocholecalciferol exhibited an average $ED_{50}$=0.5 μM.

1α-fluoro-25-hydroxy-16-ene-23-yne-26,27-hexafluorocholecalciferol exhibited an average $ED_{50}$=0.1 μM.

The useful activity of compounds of formula I as agents for the treatment of neoplastic diseases, such as leukemia, can be demonstrated by the following test procedures.

HL-60 Differentiation Assay:

The HL-60 tumor cell line was originally derived from a patient with promyleocytic leukemia and purchased from American Type Culture Collection (ATCC CCL240). The cells are maintained in suspension using the media RPMI 1640 (Gibco catalog #320–1875) plus 20% heat inactivated fetal bovine serum (FBS). For experiments, cells are diluted to 200,000 cells/ml in 5 ml of media in 25 cm$^2$ flasks. Compounds were typically tested at four concentrations in duplicate flasks. Control flasks were supplemented with vehicle alone at the highest concentration such as 0.1% ethanol. Flasks are incubated upright for 4 days in 5% $CO_2$ at 37° C. On day 4, a 1 ml aliquot of cells was centrifuged, the media removed and the cells resuspended in a 0.2 ml of solution of nitroblue tetrazolium/phorbol 12 myristate 13-acetate (NBT/TPA) in media prepared as follows. Nitroblue tetrazolium is dissolved in media at 1 mg/ml. To this solution is added TPA to a final concentration of 100 ng/ml. The cells are suspended and incubated at 37° C. for 30 min. prior to transferring to ice. An aliquot is removed and a total of 200 cells is counted using a hemocytometer. Cells without pigmented granules are Judged to be undifferentiated while those containing blue black formazan (indicating conversion of NBT) granules were scored as differentiated. Results are expressed as percent differentiated cells by calculating the ratio of the number of dark cells per total number of cells counted. The results are set forth below in Tables IIA and IIB.

TABLE IIA

| | % Differentiated Cells | | | | |
|---|---|---|---|---|---|
| | $10^{-10}$ | $10^{-9}$ | $10^{-8}$ | $10^{-7}$ | $10^{-6}$ |
| 1,25-dihydroxy-16-ene-23-yne-26,27-hexafluorocholecalciferol | | 64 | 89 | 91 | 90 |
| 25-hydroxy-16-ene-23-yne-26,27-hexafluorocholecalciferol | NT | 15 | 18 | 72 | 88 |
| 1α-fluoro-25-hydroxy-16-ene-23-yne-26,27-hexafluorocholecalciferol | NT | 61 | 90 | 93 | 96 |
| 1,25-dihydroxy-16-ene-23-yne-26,27-hexafluoro-19-nor-cholecalciferol | 1.5 | 56.5 | 89.5 | NT | NT |

NT means not tested.

1,25-dihydroxy-16-ene-23-yne-26,27-hexafluorocholecalciferol exhibited an average $ED_{50}$ (Dose that would induce at least 50% of cells to differentiate)=<1 nM.

25-hydroxy-16-ene-23-yne-26,27-hexafluorocholecalciferol exhibited an average $ED_{50}$=35 nM.

1α-fluoro-25-hydroxy-16-ene-23-yne-26,27-hexafluorocholecalciferol exhibited an average $ED_{50}$=<1 nM.

1,25-dihydroxy-16-ene-23-yne-26, 27-hexafluoro-19-nor-cholecalciferol exhibited an average $ED_{50}$=0.8 nM.

Additional tests were conducted on the following compounds for which the results are provided in Table IIB.

TABLE IIB

| | % Differentiated Cells | | | | | | | |
|---|---|---|---|---|---|---|---|---|
| | $10^{-10}$ | $3 \times 10^{-10}$ | $10^{-9}$ | $3 \times 10^{-9}$ | $10^{-8}$ | $3 \times 10^{-8}$ | $10^{-7}$ | $10^{-6}$ |
| 1,25-dihydroxy-16-ene-23-yne-26,27-hexafluoro-cholecalciferol | 4 | 17 | 66.5 | 92.5 | 94.5 | 95.5 | NT | NT |
| 25-hydroxy-16-ene-23-yne-26,27-hexafluoro-cholecalciferol | NT | NT | 16 | NT | 43 | NT | 85 | 92 |

The useful activity of compounds of formula I as agents for the treatment of sebaceous gland diseases, such as acne and seborrheic dermatitis, can be demonstrated by the following test procedure.

Sebaceous cells are isolated from adult human sebaceous glands, derived from facial skin removed during cosmetic surgery, and cultured on a layer of mouse 3T3 fibroblasts. This method involves the separation of the epidermal layer from the dermis by an electrokeratome. The dermal tissue is then treated, by enzymatic and mechanical methods, to generate a single cell suspension of sebaceous cells.

The cells are cultured in Iscove's medium containing 10% fetal calf serum and 4 μg/ml dexamethasone.

Cells are plated in medium without the test compound and then given the compound in fresh medium 24–48 hours after the initial plating. The cultures are given fresh medium, containing the test compound, every 48 hours. On the day of harvesting, the cultures are rinsed with 0.03% ethylenediamine tetraacetic acid (EDTA) in phosphate buffered saline (PBS), to remove only the 3T3 fibroblasts. The remaining sebocyte colonies are incubated in 0.05% trypsin/0.03% EDTA to create a single cell suspension of sebocytes. The cells are diluted, mixed vigorously to maintain a single cell suspension, and counted in a hemocytometer.

All compounds are handled in the following manner. Stock solutions are made up as $10^{-2}$M solutions in degassed 100% ethanol and stored at $-20°$ C. in the dark. Solutions are never used after storage of more than a month. During experimental use the solutions, which have been aliquoted, are thawed once and used by diluting directly into complete medium to the appropriate concentration, at, $10^{-7}$, $10^{-8}$ and $10^{-9}$M.

The compounds were tested for the inhibition of proliferation of sebaceous cells in vitro at the following concentrations: $10^{-7}$, $10^{-8}$ and $10^{-9}$M.

The results are summarized in Table III below as the amount of compound necessary to inhibit the proliferation of the sebaceous cells by 50% as compared to a control, diluent treated only, culture ($ID_{50}$).

TABLE III

| Compound | $ID_{50}$ (μM) |
|---|---|
| 1,25-dihydroxy-16-ene-23-yne-26,27-hexafluorocholecalciferol | <0.01 |
| 25-hydroxy-16-ene-23-yne-26,27-hexafluorocholecalciferol | 0.05 |
| 1α-fluoro-25-hydroxy-16-ene-23-yne-26,27-hexafluorocholecalciferol | 0.001 |

Oral dosage forms comprising compounds of formula I of the invention may be incorporated in capsules, tablets and the like with pharmaceutically acceptable carrier materials.

Illustrative of the pharmaceutically acceptable carrier materials which may be incorporated into capsules, and the like are the following: a binder such as gum tragacanth, acacia, corn starch, or gelatin; an excipient such as dicalcium phosphate, a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, adsorbable, water-soluble and emulsion-type bases such as petrolatum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the inflammation for the exertion of local action. Accordingly, the topical compositions include those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials. In addition to application to the skin, the topical compositions of this invention can also be employed in the treatment of inflammations of mucous membranes, where such membranes are accessible to topical application of medication. For example, the topical composition can be applied to the mucous lining of the mouth or lower colon.

EXAMPLE 1

[3aS-[3(S*),3[3aα,7α,7aβ]]-1,1,1-Trifluoro-6[3a,4,5,
6,7,7a-hexahydro-3a-methyl-7-[(trimethylsilyl)oxy]-
1H-inden-3-yl]-2-(trifluoro-methyl)-3-heptyn-2-ol In a 50 ml heart-shaped flask fitted with a gas inlet was placed a solution of (1.79 mmole) 522 mg of [3aS-[3(S*), 3aα,7α,7aβ]]-[[3a,4,5,6,7,7a-hexahydro-3a-methyl-3-(1-methyl-3-butynyl)-1H-inden-7-yl]oxy]trimethylsilane in 15 ml of anhydrous tetrahydrofuran. After cooling at −75° C., 1.85 ml (2.96 mmole) of 1.6M solution of n-butyllithium in hexane was added dropwise over 5 minutes and the mixture was stirred at −75° C. for 30 min. Then a stream of hexafluoroacetone was bubbled into the mixture for 15 min with temperature maintained at −75° C. The reaction mixture was stirred for one additional hour, and then quenched with 1:1 mixture of 2M KHCO$_3$ and 1M Rochelle salt added dropwise. The mixture was stired at room temperature for one hour and then diluted with 25 ml of the same salt solution. After extraction with 4×100 ml of CH$_2$Cl$_2$, the organic phase was washed with 50 ml of the same salt solution, dried (Na$_2$SO$_4$) and evaporated. The oily residue was azeotroped with benzene to give 2.38 g of crude oily product. Purification was performed by flash chromatography (ethylacetate (EtOAc)-hexane 1:9) to give 817 mg (100%) of the title compound as an oil; $[\alpha]_D^{25}$+41.0 (c 0.20 CHCl$_3$); $^1$H NMR (CDCl$_3$): δ0.07 (s, 9H), 1.01 (s, 3H), 1.10 (d, J=8 Hz, 3H), 2.15–2.50 (m, 4H), 3.00 (s, 1H), 4.08 (br s, 1H), 5.36 (br s, 1H).

EXAMPLE 2

[3aR-[1(R*),3aα,4β,7aβ]]-3,3a,5,6,7,7a-Hexahydro-
7a-methyl-1-[6,6,6-trifluoro-5-hydroxy-1-methyl-5-
(trifluoromethyl)-3-hexynyl]-4H-inden-4-ol Into a 100 ml flask with a gas inlet tube was placed a solution of 812 mg (1.78 mmole) of [3aS-[3(S*),3aα,7a, 7aβ]]-1,1,1-trifluoro-6[3a,4,5,6,7,7a-hexahydro-3a-methyl-7-[(trimethylsilyl)oxy]-1H-inden-3-yl]-2-(trifluoromethyl)-3-heptyn-2-ol in 18 ml of anhydrous tetrahydrofuran. To this was added 5.34 ml (5.34 mmole) of tetra-butylammonium fluoride in tetrahydrofuran, and the mixture was stirred at room temperature under argon for 80 min. The reaction was then quenched by addition of 9 ml of half-saturated NaHCO$_3$ and stirred at room temperature for an additional 20 min. Excess of tetrahydrofuran was removed by evaporation and additional 9 ml of bicarbonate was added. The mixture was extracted with 3×120 ml ethyl acetate, the extract was washed with brine, dried (Na$_2$SO$_4$) and evaporated to give 890 mg of crude product. After purification by flash chromatography (EtOAc-hexane 1:2), it gave 690 mg of the compound, which was crystallized from pentane: 546 mg (79.8%), m.p. 109°–111° C. (in addition of 90 mg of partially crystalline mother liquors); $[\alpha]_D^{25}$+19.3° (c0.29, CHCl$_3$); $^1$H-NMR(CDCl3): δ1.07 (s,3H), 1.11 (d,J=8 Hz,3H), 2.01 (m,1H), 2.20–2.53 (m,4H), 4.19 (br s,1H), 5.41 (br s,1H).

EXAMPLE 3

[3aR-[1(R*),3aα,4β,7aβ]]-3,3a,5,6,7,7a-Hexahydro-
7a-methyl-1-[6,6,6-trifluoro-5-hydroxy-1-methyl-
5(trifluoro-methyl)-3-hexynyl]-4H-inden-4-one In a 25 ml heart-shaped one-necked flask fitted with a gas inlet tube was placed a solution of 100 mg (0.26 mmole) of [3aR-[1(R*), 3aα,4β,7aβ[[-3,3a,5,6,7,7a-hexahydro-7a-methyl-1-[6,6,6-trifluoro-5-hydroxy-1-methyl-5-(trifluoromethyl)-3-hexynyl]-4H-inden-4-ol in 6 ml of anydrous CH$_2$Cl$_2$. To this was added at room temperature, 176 mg (0.8 mmole) of pyridinium chlorochromate in several portions, and the mixture was stirred at room temperature for 50 min under argon. To this mixture was then added 9 ml of ether in portion and stirring in the course of 10 min, then filtered and the filtrate evaporated to dryness. 117 mg of crude product thus obtained was purified by chromatography on silicagel column with ethyl acetate-hexane 1:3 to give the title compound 73 mg (73.4%) as amorphous solid; $[\alpha]_D^{25}$+ 35.3° (c 0.15, CHCl$_3$); 1H-NMR (CDCl$_3$): δ0.84 (s, 3H), 1.17 (d, J-8Hz, 3H), 1.70–1.95 (m, 2H), 1.86–1.95 (m,1H), 2.85 (m, 1H), 3.10 (s, 1H), 5.40 (bs 1H).

EXAMPLE 4

1,25-Dihydroxy-16-ene-23-yne-26,27-hexafluoro-
cholecalciferol

In a 50 ml egg-shaped flask fitted with a gas inlet was placed a solution of 333 mg (0.571 mmole) of [3S-(3α, 5β,Z)]-2-[2-[2-methylene-3,5-bis[[(1,1-dimethylethyl)dimethylsilyl]oxy]cyclohexylidene]ethyl]diphenyl phosphine oxide in 7 ml anhydrous tetrahydrofuran. To this was added at −75° C., 0.325 ml (0.521 mmole) of 1.6M n-butyllithium in hexane dropwise under argon, when a red color of reaction mixture developed. After stirring for 6 min, a solution of 73 mg (0.191 mmole) of [3aR-[1(R*),3aα,7aβ] ]-3,3a,5,6,7,7a-hexahydro-7a-methyl-1-[6,6,6-trifluoro-5-hydroxymethyl-5-(trifluoromethyl)-3-hexynyl]-4H-inden-4-one in 5 ml anhydrous tetrahydrofuran was added dropwise over 15 min period. The reaction mixture was stirred for 1 hour in dark at −75° C., and then quenched with 2.6 ml of 1:1 mixture of 2N Rochelle salt and 2N KHCO$_3$ solutions and was allowed to warm to room temperature. It was then diluted with 10 ml of the same salt solution and extracted with 3×60 ml ethyl acetate. The extract was washed with 3×30 ml brine, dried (Na$_2$SO$_4$) and evaporated. The crude intermediate was purified by flash chromatography on silica gel column with ethyl acetate-hexane 1:5 to give 93 mg (65.2%) of the disilyl-protected title compound.

In a 25 ml dark wall heart-shaped flask fitted with a gas inlet was placed 92 mg (0.123 mmole) of the disilylprotected title compound in 5 ml anhydrous tetrahydrofuran. To this was added 0.89 ml (0.89 mmole) of 1M tetrabutylammonium fluoride in tetrahydrofuran, and the mixture was stirred for 16 hrs under argon. The reaction was then quenched with 3 ml of half-saturated NaHCO$_3$ and stirred 20 min at room temperature. It was then extracted with 3×50 ml of ethyl acetate. The extract was washed with 2×15 ml of half-saturated NaHCO$_3$ and 15 ml of brine, dried (Na$_2$CO$_3$) and evaporated. The crude product was purified by flash chromatography with ethyl-acetate 4:1, to give 57 mg (89.4%) of the title compound as a foamy glass; $[\alpha]_D^{25}$+59.1° (c 0.11, CH$_3$OH); $^1$H-NMR(CDCl$_3$): δ-0.71 (s,3H), 1.14 (d, J=8 Hz,3H), 2.61 (m, 1H), 2.83 (m, 1H), 3.20 (brs, 1H), 4.25-(br s, 1H), 4.26(br s, 1H), 5.02 (s, 1H), 5.35 (s,1H),5.42 (s, 1H), 6.10 (d, J=12 Hz, 1H), 6,38 (d, J=12 Hz, 1H); UVmax (ethanol) 263 nm.

EXAMPLE 5

25-Hydroxy-16-ene-23-yne-26,27-hexafluoro-chole-
calciferol

In a 50 ml egg-shaped flask fitted with a gas inlet was placed a solution of 273 mg (0.604 mmole) of [5S-Z]-2-[2-[2-methylene-5-[[(1,1-dimethylethyl)dimethylsilyl]oxy]cyclohexylidene]ethyl]diphenyl phosphine oxide in 6.4 ml anhydrous tetrahydrofuran. To this was added, at −75° C., 0.343 ml (0.548 mmole) of 1.6M n-butyl lithium in hexane dropwise under argon, until red color of the reaction mixture developed. After stirring for 6 min, a solution of 83 mg (0.217 mmole) of [3aR-[1(R*),3aα,7aβ]]-3,3a,5,6,7,7a-hexahydro-7a-methyl-1-[6,6,6-trifluoro-5-hydroxy-1-methyl-5-(trifluoromethyl)-3-hexynyl]-4H-inden-4-one in 6.5 ml of anhydrous tetrahydrofuran was added dropwise over 23 min period. This reaction mixture was stirred in dark for 1 hr 15 min, and then quenched with 2.7 ml of a 1:1 mixture of 2N Rochelle salt and 2M KHCO$_3$ at −75° C., and allowed to warm up to room temperature. It was diluted with 10.5 ml of the same salt mixture and extracted with 3×65 ml ethyl acetate. The extract was washed with 3×32 ml of saturated brine, dried (Na$_2$SO$_4$) and evaporated. This crude silyl protected title compound was purified by flash chromatography on silica gel with ethyl acetate-hexane 1:5 to give 78 mg (58.3%) of the silylated intermediate. In a 25 ml flask fitted with a gas inlet, was placed a solution of 76 mg (0.123 mmole) of the silyl intermediate in 3.5 ml anhydrous tetrahydrofuran. To this was added 0.70 ml (0.70 mmole) of 1M solution of tetrabutyl ammonium fluoride in tetrahydrofuran, and the reaction mixture was stirred at room temperature for 16 hrs. It was then quenched with 2.5 ml of half-saturated NaHCO$_3$ and stirred at room temperature for 15 min. The mixture was extracted with 3×35 ml ethyl acetate, and the extract was washed with 2×12 ml of half-saturated NaHCO$_3$ and 14 ml brine, dried ((Na$_2$SO$_4$) and evaporated. The crude product was purified by flash chromatography with ethyl acetate-hexane 1:1 to give 49 mg (79.3%) of the title compound; $[\alpha]_D^{25}$+77.3°(c0.15, CH$_3$OH) 1H-NMR(CDCl$_3$): δ0.72(s,3H), 1.13 (d, J=8 Hz, 3H), 2.57 (m, 1H), 2.82 (m, 1H), 3.95 (br s, 1H), 4.84 (s, 1H), 5.07 (s, 1H), 6.12 (d, J=12 Hz, 1H), 6.23 (d, J=12 Hz, 1H), UV max (ethanol) 263 nm.

EXAMPLE 6

1α- fluoro-25-hydroxy-16-ene-23-yne-26,27-hexafluoro-cholecalciferol

In a 50 ml egg-shaped flask fitted with a gas inlet was placed a solution of 159 mg (0.338 mmole) of [3S-(3α,5β, Z)]-2-[2-[2-methylene-3-fluoro-5-[[(1,1-dimethylethyl)dimethylsilyl]oxy]cyclohexylidene]ethyl]diphenyl phosphine oxide in 4.3 ml anhydrous tetrahydrofuran. To this was added, at −75° C., 0.201 ml (0.322 mmole) of 1.6M n-butyllithium in hexane dropwise under argon, until red color of the reaction mixture developed. After stirring for 6 min, a solution of 47 mg (0.12 mmole) of [3aR-[1(R*),3aα, 7aβ]]-3,3a,5,6,7,7a-hexahydro-7a-methyl-1-[6,6,6-trifluoro-5-hydroxy-1-methyl-5-(trifluoromethyl)-3-hexynyl]-4H-inden-4-one in 2.5 ml of anhydrous tetrahydrofuran was added dropwise. This reaction mixture was stirred in dark for 1 hr 15 min, and then quenched with a 1:1 mixture of 2N Rochelle salt and 2M KHCO$_3$ at −75° C., and allowed to warm up to room temperature. It was diluted with 10.5 ml of the same salt mixture and extracted with ethyl acetate. The extract was washed with saturated brine, dried (Na$_2$SO$_4$) and evaporated. This crude silyl protected title compound was purified by flash chromatography on silica gel with ethyl acetate-hexane 1:5 to give 27 mg (35%) of the silylated intermediate.

In a 25 ml flask fitted with a gas inlet, was placed a solution of 27 mg (0.0425 mmole) of the silyl intermediate in 1.8 ml anhydrous tetrahydrofuran. To this was added 0.257 ml (0.257 mmole) of 1M solution of tetrabutyl ammonium fluoride in tetrahydrofuran, and the reaction mixture was stirred at room temperature for 16 hrs. It was then quenched with half-saturated NaHCO$_3$ and stirred at room temperature for 20 min. The mixture was extracted with ethyl acetate, and the extract was washed with half-saturated NaHCO$_3$ and brine, dried (Na$_2$SO$_4$) and evaporated. The crude product was purified by flash chromatography with ethyl acetate-hexane 1:1.3 to give 19 mg (86%) of the title compound as a glass; $[\alpha]_D^{25}$+71.7° (c0.12, CH$_3$OH) 1H-NMR(CDCl$_3$): δ0.72 (s, 3H), 1.15 (d, J=8 Hz,3H), 2.63 (m, 1H), 2.82 (m, 1H), 4.23 (br s, 1H), 5.12 (s, 1H), 5.14 (dm, J=48 Hz, 1H), 5.41 (s,1H), 6.12 (d, J-12 Hz, 1H), 6.40 (d, J=12 HZ, 1H).

EXAMPLE 7

1,25-Dihydroxy-16-ene-23-yne-26,27-hexafluoro-19-nor-cholecalciferol

In a 50 ml egg-shaped flask fitted with a gas inlet was placed a solution of 605 mg (1.06 mmole) of [3R-(3α,5β, Z)-3,5-bis[[(1,1-dimethylethyl)dimethylsilyl]oxy]cyclohexylidene]ethyl]diphenyl phosphine oxide in 7 ml anhydrous tetrahydrofuran. To this was added at −75° C., 0.645 ml (1.05 mmole) of 1.6M n-butyllithium in hexane dropwise under argon, when a red color of reaction mixture developed. After stirring for 6 min, a solution of 162 mg (0.424 mmole) of [3aR-[1(R*),3aα,7aβ]]-3,3a,5,6,7,7a-hexahydro-7a-methyl-1-[6,6,6-trifluoro-5-hydroxy-methyl-5-(trifluoromethyl)-3-hexynyl]-4H-inden-4-one in 4.5 ml anhydrous tetrahydrofuran was added dropwise over 15 min period. The reaction mixture was stirred for 1 hour in dark at −75° C. and then quenched with 2.6 ml of 1:1 mixture of 2N Rochelle salt and 2N KHCO$_3$ solutions and was allowed to warm to room temperature. It was then diluted with 10 ml of the same salt solution and extracted with 3×60 ml ethyl acetate. The extract was washed with 3x30 ml brine, dried (Na$_2$SO$_4$) and evaporated. The crude intermediate was purified by flash chromatography on silica gel column with ethyl acetate-hexane 1:8 to give 168 mg of the disilyl-protected title compound. In a 25 ml dark wall heart-shaped flask fitted with a gas inlet was placed 168 mg (0.229 mmole) of the disilylprotected title compound in 4.5 ml anhydrous tetrahydrofuran. To this was added 2.7 ml of 1M tetrabutylammonium fluoride in tetrahydrofuran, and the mixture was stirred for 43 hrs under argon. The reaction was then quenched with 5 ml of water and stirred 25 min at room temperature. It was then extracted with 3×100 ml of ethyl acetate. The extract was washed 4 times with brine, dried (Na$_2$SO$_4$) and evaporated. The crude product was purified by flash chromatography with ethyl-acetate-hexane 3:1 to give 99 mg of title compound as foam: $[\alpha]_D^{25}$+25° C. (cO.2 ethanol).

EXAMPLE 8

25-Hydroxy-16-ene-23-yne-26,27-hexafluoro-19-nor-cholecalciferol

The title compound can be prepared in a manner analogous to the procedure described in Example 5 by using [5S-Z]-5-[[(1,1-dimethylethyl)dimethylsilyl]oxy]cyclohexylidene]ethyl]diphenyl phosphine oxide instead of [5S-Z]-2-[2-[2-methylene-5-[[(1,1dimethylethyl)dimethylsilyl] oxy]cyclohexylidene]ethyl]diphenyl phosphine oxide.

EXAMPLE 9

1α-Fluoro-25-hydroxy-16-ene-23-yne-26,27-hexafluoro-19-nor-cholecalciferol

The title compound can be prepared in a manner analogous to the procedure described in Example 6 by using [3R-(3α,5β,Z)]-3-fluoro-5[[(1,1-dimethylethyl)dimethylsilyl]oxy]cyclohexylidene]ethyl]diphenyl phosphine oxide instead of [3S- (3α,5β, Z)]-2-[2-[2-methylene-3-fluoro-5[[(1,1-dimethylethyl)dimethylsilyl]oxy]cyclohexylidene]ethyl]diphenyl phosphine oxide.

EXAMPLE 10

| Oral Dosage Form Soft Gelatin Capsule | |
|---|---|
| | mg/Capsule |
| Compound A | 0.0001–0.010 |
| Butylated Hydroxytoluene (BHT) | 0.016 |
| Butylated Hydroxyanisole (BHA) | 0.016 |
| Fractionated Coconut Oil (Neobee M-5) | 160.0 |

1. Suspend the Butylated Hydroxytoluene and Butylated Hydroxyanisole in fractionated coconut oil. Warm to about 50° C. and stir until dissolved.
2. Blanket the solution in step 1 with nitrogen and add Compound A. Stir until Compound A has dissolved, maintaining the nitrogen blanket.
3. Fill in soft gelatin capsules Compound A is 25-hydroxy-16-ene-23-yne-26,27-hexafluorocholecalciferol.

EXAMPLE 11

| Topical Cream | |
|---|---|
| | mg/gm |
| Compound A | 0.001–1.0 |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA | 0.05 |
| Sorbitol Solution | 2.0 |
| Edetate Disodium | 0.01 |
| Methylparaben | 0.18 |
| Distilled Water | q.s. to 100 gm |

1. Melt the Cetyl Alcohol, Stearyl Alcohol, Sorbitan Monostearate, Glyceryl Monostearate and Polyoxyethylene Stearate Blend, Polysorbate 60, Mineral Oil and a portion (60%) of Propylene Glycol together in a stainless steel container at 70° C. in a water bath.
2. Dissolve Butylated Hydroxyanisole and Propylparaben in the material from step 1 and maintain at 70°–72° C. Record the temperature of the melt.
3. Heat the Sorbitol Solution and the water in a suitable container at 70°–75° C.
4. Add the Edetate Disodium and Methylparaben to the solutions in step 3 and mix until dissolved. Record the temperature of the aqueous phase.
5. Dissolve the appropriate amount of Compound A in another portion (30%) of the Propylene Glycol in a beaker and add this to the material from step 2 while mixing. Rinse the container with the remaining (10%) of the Propylene Glycol and add this to the mixture from step 2. Maintain a nitrogen atmosphere above the product during this and subsequent steps.

NOTE:

Once Compound A is added, steps 5 and 6 must be completed in rapid succession.

6. Add the oil phase from step 2 to the aqueous phase from step 5 while emulsifying with a high shear mixer. Rinse the oil phase container by withdrawing a portion of the emulsion and add this immediately to the rest of the emulsion.
7. Continue mixing and allow the product to cool to 50°–55° C. Remove an aliquot for determination of water content and droplet size. Record the result. Add additional water if necessary.
8. Continue mixing with a paddle mixer until the product cools to room temperature. Record the weight of the final product.
9. Transfer the cream to appropriate containers.

NOTE:

1. The manufacturing has to be done in amber light.
2. The final cream should be packaged within 7 days from completion of its manufacture.

We claim:

1. A method for the treatment of sebaceous gland diseases which comprises administering to a host in need of such treatment an effective amount of a compound of formula

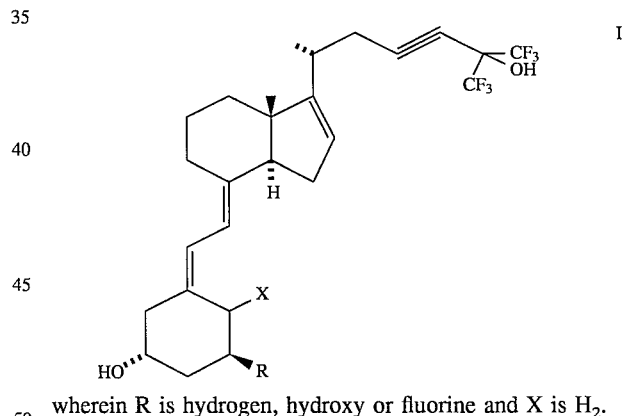

wherein R is hydrogen, hydroxy or fluorine and X is $H_2$.

2. The method in accordance with claim 1, wherein R is hydroxy or fluorine.
3. The method in accordance with claim 1, wherein the sebaceous gland disease is acne.
4. The method in accordance with claim 1, wherein the compound of formula I is administered orally.
5. The method in accordance with claim 1, wherein the compound of formula I is administered topically.
6. The method in accordance with claim 1, wherein the compound of formula I is 26,26,26,27,27,27-hexafluoro-1,25-dihydroxy-16-ene-23-yne-19-nor-cholecalciferol.

* * * * *

UNITED STATES PATENT AND TRADEMARK OFFICE
CERTIFICATE OF CORRECTION

PATENT NO. : 5,612,328
DATED : March 18, 1997
INVENTOR(S) : Baggiolini, et al.

It is certified that error appears in the above-indentified patent and that said Letters Patent is hereby corrected as shown below:

On title page, item [75] Inventor's Names: "Barbara J. Baggiolini, North Caldwell; Shian-Jan Shiuey, Nutley; Milan R. Uskokovic, Upper Montclair, all of NJ". The Inventor information should read --- Enrico Giuseppe Baggiolini, deceased, by executrix Barbara J. Baggiolini, North Caldwell; Shian-Jan Shiuey, Nutley; Milan R. Uskokovic, Upper Montclair, all of NJ --- .

Signed and Sealed this

Twenty-fourth Day of June, 1997

Attest:

BRUCE LEHMAN

*Attesting Officer*  *Commissioner of Patents and Trademarks*